United States Patent [19]

Goldstein

[11] Patent Number: 5,586,163
[45] Date of Patent: Dec. 17, 1996

[54] CATHETERIZATION PROCEDURE PLATFORM SYSTEM AND METHOD

[76] Inventor: James A. Goldstein, 1645 Hillwood Dr., Bloomfield Hills, Mich. 48304

[21] Appl. No.: 286,512

[22] Filed: Aug. 5, 1994

[51] Int. Cl.⁶ .................................................. H05G 1/00
[52] U.S. Cl. ............................ 378/204; 378/208; 211/13; 211/126
[58] Field of Search ............................ 378/41, 42, 195, 378/208, 209, 204, 210, 177, 190; 211/13, 126; 206/570, 370, 438, 563, 564; 5/611, 613

[56] References Cited

U.S. PATENT DOCUMENTS

| | | | |
|---|---|---|---|
| 4,046,254 | 9/1977 | Kramer | 206/370 |
| 4,266,669 | 5/1981 | Watson | 206/564 |
| 4,635,914 | 1/1987 | Kabanek | 269/328 |
| 5,185,778 | 2/1993 | Magram | 378/196 |
| 5,281,400 | 1/1994 | Berry, Jr. | 206/370 |

*Primary Examiner*—Don Wong
*Attorney, Agent, or Firm*—Neal Kalishman

[57] ABSTRACT

A platform which is mounted over the fluoroscopic table in a catheterization procedure. The platform contains compartments for diagnostic or therapeutic catheterization procedure dependent devices, supplies, wastes, or fluids. The platform is mounted on a vertical support structure and utilizes removable inserts that fit within the compartments.

27 Claims, 3 Drawing Sheets

CATHETERIZATION PROCEDURE PLATFORM SYSTEM AND METHOD

BACKGROUND OF THE INVENTION

1. Field of the Invention

The invention relates to catheterization procedures and systems. In particular, it relates to a platform for holding supplies, devices, waste and fluids in front of the operator and over the patient.

2. Description of the Prior Art

Invasive vascular catheterization procedures employ numerous sterile equipment items to facilitate insertion of catheters through the skin and into big vessels of various organs for purposes of diagnosis by injection of contrast dyes, sampling of bodily fluids, removal of tissues and measurement of pressures. Such procedures are also performed for therapeutic reasons, including interventions to open blockages, ablate or remove abnormal tissue, instill medicines, etc. Such catheterization procedures are performed in sterile conditions in radiologic suites equipped with fluoroscopic/angiographic radiologic equipment. These procedures are performed with the patient lying on a fluoroscopic table and covered with sterile gowns and drapes, and performed by one or two sterilely gowned operators.

Although catheterization procedures vary according to the specific organ being investigated and as well by whether the procedure is diagnostic or therapeutic, there are basic equipment items that are common to all such procedures, these include: (1) preparatory solutions including iodine and alcohol, sterile sponges and sponge clamps, utilized to sterilely prepare the skin site for catheter entry; (2) sterile drapes and towels employed to cover the patient and thus provide a sterile field for performance of the procedure; (3) sterile drapes and sheets to cover the radiologic imaging tube and other equipment that may be upon or adjacent to the sterile field; (4) an equipment table that is used as a "staging area" for various equipment items; (5) sterile bowls for reservoirs of procedure dependent fluids (such as saline, heparin and lidocaine), and as storage receptacles for various catheterization equipment including guide wires, catheters, and various interventional devices (balloons); (6) disposable plastic syringes of various sizes for injection of procedure dependent fluids; (7) sterile 4×4's (also known as gauze pads or sponges); and (8) miscellaneous other disposable instruments including scalpel and/or scalpel blades, various size disposable needles for injection of procedure dependent fluids, hemostats and towel clamps.

To prepare for the procedure, a prepackaged "tray" containing many of the disposable equipment items enumerated (i.e. drapes, bowls, syringes, needles, hemostat, scalpel, etc., but not including the vascular access sheaths, catheters, wires or balloons) is placed on an equipment staging table (positioned near the fluoroscopy table), opened and disassembled. The patient is draped with sterile sheets, the equipment items are arranged on the equipment staging table, appropriate preparatory steps initiated (i.e. bowls filled with saline, cups with lidocaine, etc.), and the catheterization procedure is initiated. During the catheterization procedure itself, there is a near constant flow of steps and manipulations that require various pieces of equipment at various times; these motions include handling of syringes, sponges, hemostats, scalpels and syringes filled with procedure dependent fluids, as well as sheaths, wires, catheters, and interventional devices. Accordingly, there is a constant flow of motion between the operators (whose attention should be primarily and optimally would be constantly focused on the patient and the physiologic monitors for blood pressure, heart rhythm and radiologic imaging positioned next to and facing the patient), and these intermittently used equipment items. Unfortunately, as presently performed, many of the procedure dependent equipment items are kept on the equipment staging table which is nearly always positioned behind the operators. This arrangement necessitates the operators to be constantly turning around to replace or retrieve needed equipment items to perform equipment related maneuvers (access to wires, balloons and syringes, disposal of waste blood, etc.), thereby necessitating that their hands leave the primary catheterization equipment items, diverting their attention from the patient and the critical physiologic monitors, exposing the operators backs to potential radiation and interrupting what otherwise would be a much more efficient flow of the procedure. In addition, the catheters, manifold with plastic tubing, injection syringe and associated other equipment items (pacemakers, pacemaker generators, intra-aortic balloon pumps, indeflators for interventions) are typically placed directly in the patient's "lap" while "in-use". Furthermore, the "in-use" manipulation of these devices actually occurs in the patient's lap (on their groin-legs), which is used as a procedure "platform". Also, it is not uncommon for operators to leave various equipment items (such as needles, scalpels, syringes, sponges, sheaths, wires, etc.) not immediately "in-use" in the patient's "lap", these equipment items being left there in great part because constant turning around to replace and retrieve these items disrupts the flow of the procedure. A fundamental principle of such procedures is that efficiency in time and economy of motion facilitates performance of the procedure itself, thereby translating into better patient outcomes, particularly in critically ill patients and/or in those with very complex procedures in which efficiency of time and motion is essential to procedural success. Furthermore, given the high volume of cases performed in most laboratories, and the complex, demanding and often time-consuming nature of such studies, improvements in economy of motion and procedure time could potentially benefit "throughput" in the laboratory, and thereby be more economical.

Therefore, there is a need for a catheterization procedure equipment management system that would facilitate more efficient interaction of the operators with the various procedure dependent equipment items. Specifically, there is need for a system that would allow the operators to always be facing the patient and the physiologic monitors, with the equipment items within easy hands reach without turning around, without losing manual contact with the primary procedure dependent equipment (catheters, wires, balloons, etc.) nor losing contact with the critical safety net of the patient's physiologic and radiologic imaging monitors.

SUMMARY OF THE INVENTION

A catheterization system which comprises a fluoroscopic table, fluoroscope, and a platform for holding procedure dependent devices, supplies, fluids and waste. A method for utilizing said platform. A platform used in the method which has compartments for holding said procedure dependent devices, supplies, fluids and waste.

BRIEF DESCRIPTION OF THE DRAWINGS

FIG. 4 illustrates the platform of the invention mounted over a fluoroscopic table.

DESCRIPTION OF THE PREFERRED EMBODIMENTS

Figure 1:
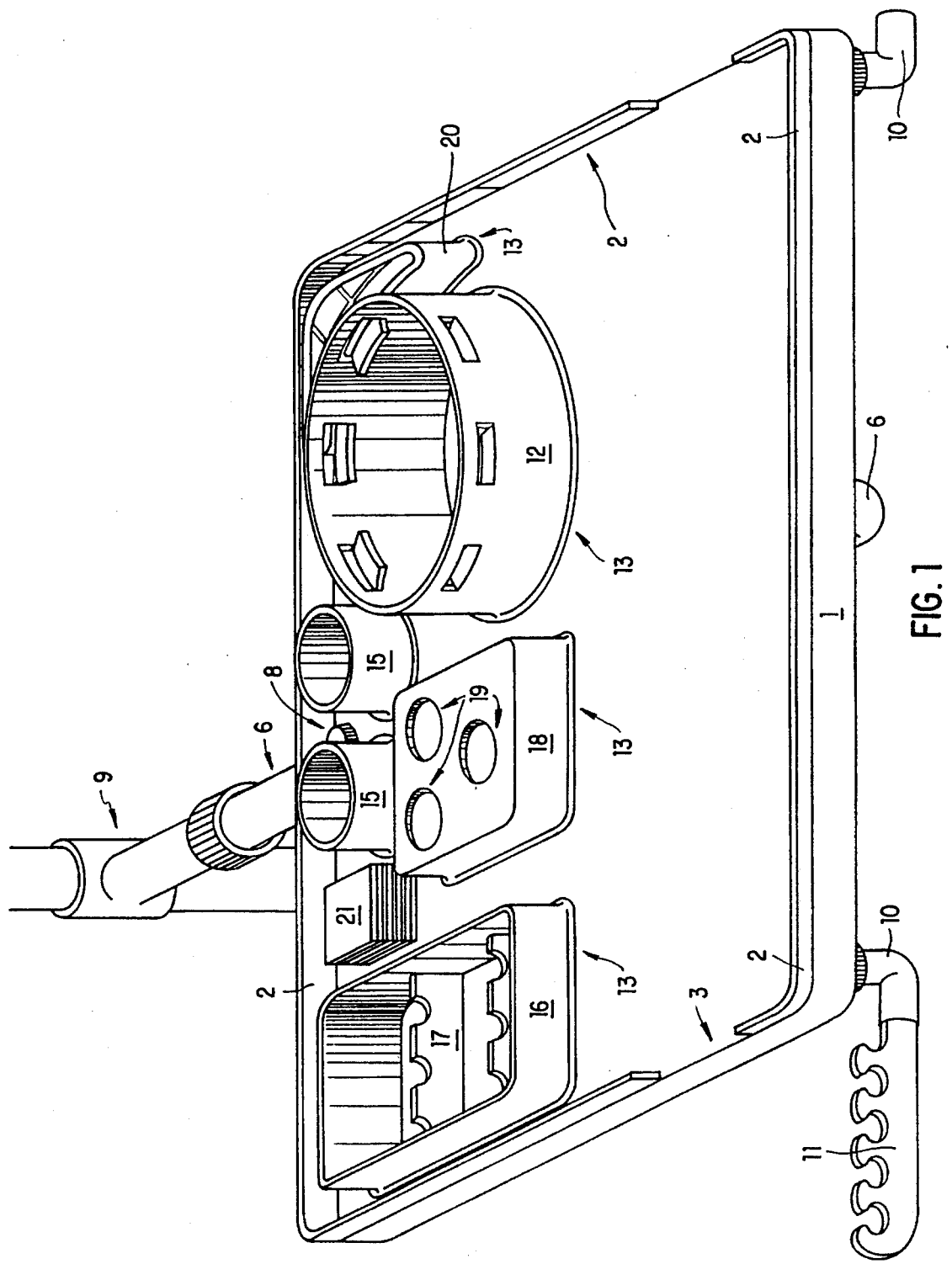
FIG. 1 is a perspective view of a fully equipped and deployed rectangular platform of the invention with disposables included.
Figure 2:
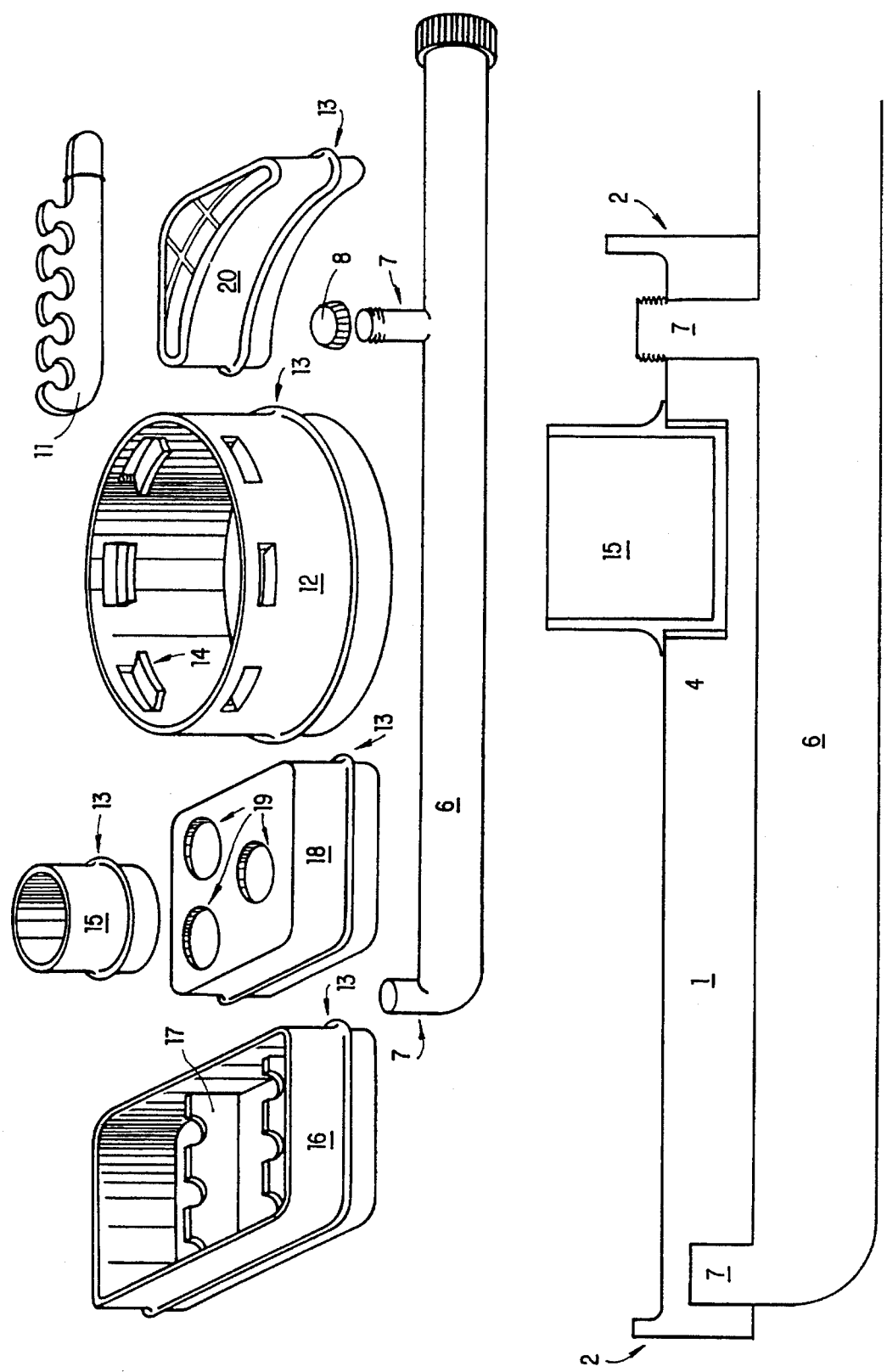
FIG. 2 illustrates various removable compartments of the invention.
Figure 3:
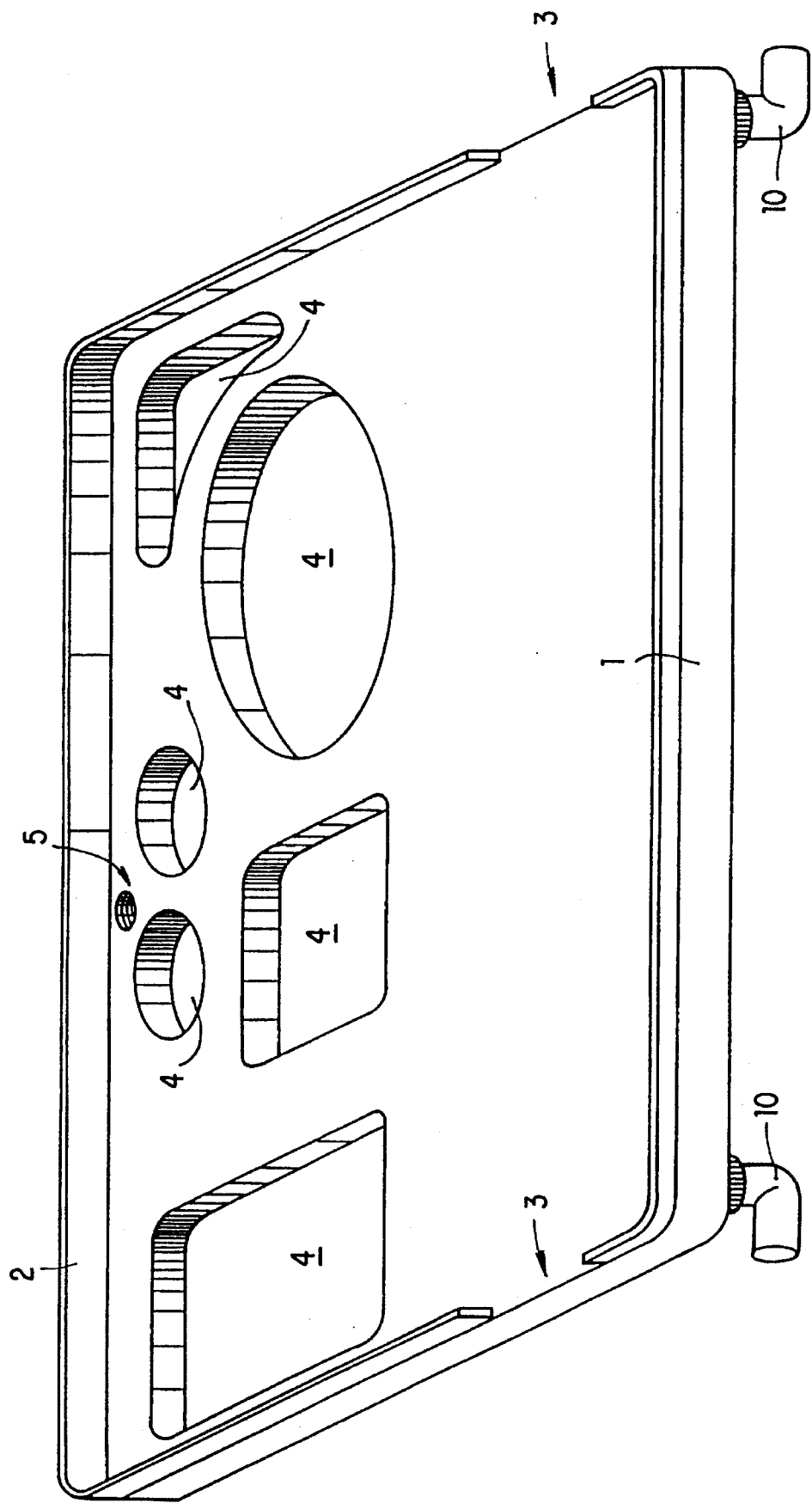
FIG. 3 is an illustration of the re-usable platform and clamp swivels.

The procedure platform system is designed to provide an equipment staging table (platform)[1] that connects directly or indirectly to the catheterization fluoroscopy table; said platform is positioned over (but not upon) the patient's lower extremities during the catheterization procedure itself. This platform system, as shown in FIGS. 1, 2 and 3 is comprised of the following preferred embodiments: A durable plastic and radiolucent rectangular platform[1] that has an open flat surface designed to accommodate various equipment items placed at the discretion of the operator. The platform has an encircling wall[2] (to prevent objects from falling off); the wall has two parallel openings[3] on either side, to facilitate extension of a catheter to lay upon the open flat surface. The surface of the platform has molded insets which serve as specific templates for insertion of individual disposable procedure equipment items, and slots[5] for attachment to a swing arm support bar. This platform sits upon and is supported by a swing-arm[6] that has bolts[7] (protrusions) that insert into slots in the platform. One of the swing arm bolts is threaded at its distal tip to accommodate a screw nut[8] which fastens the platform to the support bar. The support arm connects to a pole[9] attached to the fluoroscopic table. Alternatively this platform can be attached to existing poles utilized for support of procedure dependent fluid reservoirs or pressure transducers. Alternatively the platform can be mounted with two side bars (sleds or legs) along its length that are parallel to the fluoroscopic table (and therefore the patient's legs) and clamp onto the side of the fluoro table itself. The undersurface of the platform is fitted with two plastic swivel arms[10] designed with connectors used for attachment of a disposable catheter tubing organizer[11] and/ or disposable catheter clamp and torque stabilizers. Alternatively the plastic swivels are disposable and snap-bolt into the platform. Disposable equipment items (may be packaged as a set) include: (A) One large plastic bowl[12] designated as a saline filled receptacle for procedure dependent items including catheters, wires, balloons, etc.; the bowl has an outer encircling seating cuff[13] (flange) that provides for greater stability within the platform insets and a more "flush" fit with the open platform surface; the bowl has inner rectangular protrusions[14] that act as a partial "lid" to keep wires and catheters from inadvertently coming out of the bowl; (B) small plastic cups[15] to be used as receptacles for procedure dependent injectable fluids such as lidocaine and heparin; the cups have an outer encircling seating cuff (flange) that provides for greater stability within the platform insets and a more "flush" fit with the open platform surface; (C) a rectangular plastic receptacle[16] with one or more racks[17] for syringes, designed to serve both as a reservoir for injectable sterile saline as well as a syringe organizer: the receptacle has an outer encircling seating cuff (flange) that provides for greater stability within the platform insets and a more "flush" fit with the open platform surface; (D) a plastic waste disposal receptacle[18] covered with a lid that has multiple circular entry ports[19] for insertion of syringes with waste to be disposed; the receptacle has an outer encircling seating cuff (flange) that provides for greater stability within the platform insets and a more "flush" fit with the open platform surface; (E) a plastic receptacle bin[20] with thick plastic foam that allows insertion and removal of "sharps" (needles, scalpels, scalpel blades) as well as a cover for later definitive disposal of these contaminated items; the receptacle has an outer encircling seating cuff (flange) that provides for greater stability within the platform insets and a more "flush" fit with the open platform surface; (F) a plastic disposable clamp-on catheter tubing organizer[11] that attaches to one of the swivel arms built into the undersurface of the platform, to be used for organizing and elevating tubing off the patient's lap, as well as channeling them off the sterile field to connect to procedure dependent fluid reservoirs and/or pressure transducers off the table. The platform also has space for disposable gauze pads[21].

The patient is prepped and draped in the usual sterile fashion. The re-usable sterilizable, autoclavable platform is attached to the pole connected to the fluoroscopy table; the platform is then covered by a sterile drape uniquely designed to fit its molding insets as a template. A sterile prepackaged disposable procedure set is then opened and the individual components (catheter bowl, procedure dependent fluid cups, saline filled syringe rack, disposal receptacle and sharps bin) separately placed in their designated insets in the platform. The catheter bowl is filled with saline, the syringe rack filled with saline and the plastic syringes filled and placed in the rack, the procedure dependent fluid cups filled with their designated fluid, the inset for sterile 4×4's filled with a stack of these gauze pads, and the tubing arm clamp-organizer connected to the side of the platform. The remainder of the instruments for catheterization (including scalpel, hemostat, towel clamps and other devices) are placed on the open staging area of the platform itself. The tubing organizer clamp and the catheter clamp are inserted into their respective swivel arms. The catheterization procedure then can proceed as traditionally performed. The connector tubing lines are secured in the tubing clamp and thereby elevated off the patient's lap and channeled off the table. The platform is positioned over the patient's lower extremities with its vertical height adjustable at the connection of the platform swing-arm to the pole clamp to the fluoroscopy table, with an additional adjust available to swing the platform out over the patient's legs and to be positioned and repositioned moment-to-moment according to the most efficient, comfortable position for the operator(s). Utilizing this system, the operator can access all the procedure dependent equipment items within the reach of one hand without having to remove the other hand from the primary catheterization equipment (sheaths, wires, catheters, balloons, etc.) connected to the patient, without having to divert their attention either from the patient or the patient's physiologic monitors.

I claim:

1. A catheterization support system which comprises:
  a) a fluoroscopic table; and
  b) a platform mounted on a vertical support structure and positioned over the fluoroscopic table which further comprises compartments adapted to hold diagnostic or therapeutic catheterization procedure dependent devices, supplies, wastes, or fluids.

2. The system of claim 1 wherein said platform is mounted on a pole extending upward from the fluoroscopic bed.

3. The system of claim 1 wherein said platform is mounted on a pole which holds fluids or pressure transducers.

4. The system of claim 1 wherein said platform is pivoted on a swing arm.

5. The system of claim 1 wherein said platform further comprises a removable bowl.

6. The system of claim 1 wherein said platform further comprises at least one removable cup.

7. The system of claim 1 wherein said platform further comprises a removable rectangular receptacle containing a syringe rack.

8. The system of claim 1 wherein said platform further comprises a removable covered receptacle with multiple circular entry ports.

9. The system of claim 1 wherein said platform further comprises a removable receptacle filled with a thick plastic foam material to accommodate easy insertion/removal of sharp instruments.

10. The system of claim 1 wherein said platform further comprises a catheter and tubing clamp.

11. A platform for holding diagnostic or therapeutic catheterization procedure dependent devices, supplies, wastes or fluids which comprises a mounting bracket contained on a vertical support structure which extends the platform over a fluoroscopic bed and a surface and holders for said procedure dependent devices, supplies, wastes or fluids.

12. The platform of claim 11 wherein said platform is mounted on a pole extending upward from the fluoroscopic bed.

13. The platform of claim 11 wherein said platform is mounted on a pole which holds fluids or pressure transducers.

14. The platform of claim 11 wherein said platform is pivoted on a swing arm.

15. The platform of claim 11 wherein said platform further comprises a removable bowl.

16. The platform of claim 11 wherein said platform further comprises at least one removable cup.

17. The platform of claim 11 wherein said platform further comprises a removable rectangular receptacle containing a syringe rack.

18. The platform of claim 11 wherein said platform further comprises a removable covered receptacle with multiple circular entry ports.

19. The platform of claim 11 wherein said platform further comprises a removable receptacle filled with a thick plastic foam material to accommodate insertion/removal of sharp instruments.

20. The platform of claim 11 wherein said platform further comprises a catheter and tubing clamp.

21. The platform of claim 11 wherein said surface has at least three compartments.

22. A method of performing diagnostic or therapeutic catheterization procedures the improvement which comprises: mounting on a vertical support structure over the fluoroscopic table a platform adapted to hold diagnostic or therapeutic catheterization procedure dependent devices, supplies, wastes or fluids.

23. The method of claim 22 wherein said platform is swung over said table from a pivot point on a pole which is vertical to the platform.

24. The method of claim 22 wherein syringes are placed on a rack on said platform prior to use.

25. The method of claim 22 wherein following use of syringes they are placed in a covered container with multiple circular entry ports.

26. The method of claim 22 wherein following contamination of needles, scalpels, or scalpel blades that are placed in a receptacle the allows easy insertion/removal, and later covering for definitive disposal.

27. The method of claim 22 wherein catheters and tubing are channeled through an organizer attached to said platform.

* * * * *